United States Patent [19]

Sueptitz

[11] Patent Number: Plant 6,590

[45] Date of Patent: Feb. 7, 1989

[54] CHRYSANTHEMUM PLANT NAMED ANTONIO

[75] Inventor: Dieter Sueptitz, Hamburg, Fed. Rep. of Germany

[73] Assignee: Ball Pan Am Plant Co., Parrish, Fla.

[21] Appl. No.: 74,481

[22] Filed: Jul. 16, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Antonio, characterized by its clear white ray floret color, with immature lime green to mature yellow disc florets; flat capitulum form and single capitulum type; nine week response; compact growth habit.

1 Drawing Sheet

The present invention comprises a new and distinct cultivar of *Chrysanthemum morifolium,* Ramat., hereinafter referred to by the cultivar name Antonio.

Antonio is a product of a planned breeding program which had the objective of creating new Chrysanthemum cultivars with clear white daisy flowers having a lime green disc, freely breaking habit, and excellent year round performance. Such traits in combination were not present in previously available commercial cultivars.

Antonio was originated from a hybridization made by Dieter Sueptitz in a controlled breeding program in Hamburg, Federal Republic of Germany, in 1977. Both the male and female parents were unnamed seedlings. Antonio was discovered and selected as one flowering plant within the progeny of the stated parentage by Dieter Sueptitz in 1978 in a controlled greenhouse environment in Hamburg, Germany.

The first act of asexual reproduction of Antonio was accomplished when vegetative cuttings were taken from the initial selection in 1978 in a controlled environment in Hamburg, Federal Republic of Germany by a technician working under formulations established and supervised by Dieter Sueptitz. Horticultural examination of selected units initiated in 1978 has demonstrated that the combination of characteristics as herein disclosed for Antonio are firmly fixed and are retained through successive generations of asexual reproduction.

The following traits have been repeatedly observed and are determined to be basic characteristics of Antonio, which in combination distinguish this Chrysanthemum as a new and distinct cultivar:

1. Daisy pot mum, flat capitulum form, single capitulum type.
2. Clear white ray florets.
3. Mature disc florets yellow, immature disc florets lime green.
4. Nine week flowering response.
5. Capitulum 6–7 cm across, ray florets up to 33 mm long and 12 mm wide.
6. Approximately 30 ray florets per capitulum.
7. Performs well in year round pot mum programs.
8. Free breaking habit.

Antonio has not been observed under all possible environmental conditions. The phenotype may vary significantly with variations in environment such as temperature, light intensity, and day length. The following observations, measurements and comparisons describe plants grown in Parrish, Fla., under greenhouse conditions which approximate those generally used in commercial practice.

Of the many commercial cultivars known to the present inventor, the most similar in comparison to Antonio is Garland, disclosed in U.S. Plant Pat. No. 3,576. In comparison to Garland, Antonio has wider ray florets, more compact habit, and the ray florets of Antonio are a true white color, as opposed to the off-white color of Garland.

The accompanying photographic drawing shows typical inflorescence and foliage characteristics of Antonio. The drawing is in black and white, which accurately depicts the ray floret color, and the disc florets of several flowers are colored to accurately depict true disc floret color.

In the following description, color references are made to the Royal Horticultural Society Colour Chart. The color values were determined at approximately noon on Sept. 24, 1986 under fluorescent light at Parrish, Fla.

Classification:

*Botanical.*—*Chrysanthemum morifolium,* Ramat., cv. Antonio.

*Commercial.*—Daisy pot.

INFLORESCENCE

A. Capitulum:

*Form.*—Flat.

*Type.*—Single.

*Diameter across face.*—6–7 cm.

B. Corolla of ray florets:

*Color (general tonality from a distance of three meters).*—White.

*Color (upper surface).*—155D.

*Color (under surface).*—155D.

C. Corolla of disc floret:

*Color (mature).*—Yellow.

*Color (immature).*—Lime green.

D. Reproductive organs:

*Androecium.*—Present in disc florets only.

*Gynoecium.*—Present in both disc and ray florets.

PLANT

A. General appearance:

*Height.*—25 cm from the edge of the pot, the height varies depending upon growing conditions.

B. Foliage:

*Color* (*upper surface*).—147A.

*Color* (*under surface*).—147B.

*Shape.*—Ovate, with cleft leaf margins.

I claim:

1. A new and distinct cultivar of Chrysanthemum plant named Antonio, as illustrated and described, and particularly characterized by its clear white ray floret color, with immature lime green to mature yellow disc florets; flat capitulum form and single capitulum type; nine week response, and its compact growth habit.

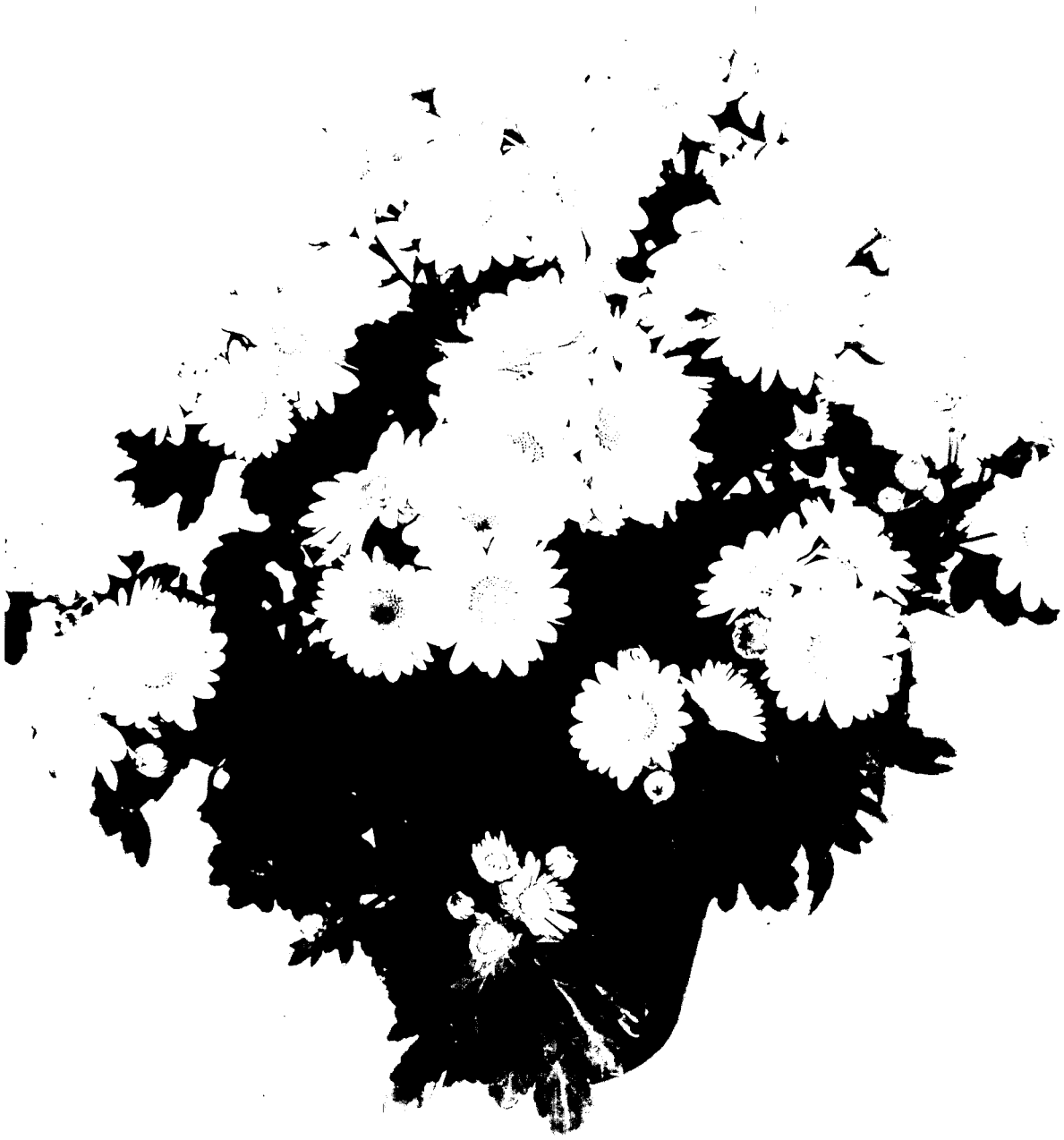

* * * * *